US012766204B2

(12) United States Patent
Frisoli et al.

(10) Patent No.: US 12,766,204 B2
(45) Date of Patent: Oct. 20, 2026

(54) METHOD FOR CONTROLLING A MOBILE ROBOTIC APPARATUS FOR DISINFECTING A SPACE AND MOBILE ROBOTIC APPARATUS FOR DISINFECTING A SPACE IMPLEMENTING SUCH METHOD

(71) Applicant: NEXT GENERATION ROBOTICS S.R.L., Pisa (IT)

(72) Inventors: Antonio Frisoli, San Giuliano Terme (IT); Massimiliano Gabardi, Merano (IT); Daniele Leonardis, Pisa (IT); Domenico Chiaradia, Pisa (IT); Luca Tiseni, Porto Recanati (IT); Massimiliano Solazzi, Cascina (IT)

(73) Assignee: NEXT GENERATION ROBOTICS S.R.L., Pisa (IT)

( * ) Notice: Subject to any disclaimer, the term of this patent is extended or adjusted under 35 U.S.C. 154(b) by 1109 days.

(21) Appl. No.: 17/683,552

(22) Filed: Mar. 1, 2022

(65) Prior Publication Data

US 2022/0273836 A1 Sep. 1, 2022

(30) Foreign Application Priority Data

Mar. 1, 2021 (IT) ........................ 102021000004727

(51) Int. Cl.
*A61L 2/10* (2026.01)
*A61L 2/24* (2006.01)
*G05D 1/00* (2024.01)

(52) U.S. Cl.
CPC *A61L 2/10* (2013.01); *A61L 2/24* (2013.01); *G05D 1/0219* (2013.01);
(Continued)

(58) Field of Classification Search
CPC .. A61L 90/00–22; A61L 2/00–28; A61L 2/10; A61L 2/24; A61L 2202/11;
(Continued)

(56) References Cited

U.S. PATENT DOCUMENTS

2012/0223216 A1* 9/2012 Flaherty ............... G05D 1/0242 901/1
2020/0179543 A1 6/2020 Deshays et al.

FOREIGN PATENT DOCUMENTS

EP 3033115 A1 6/2016
WO WO-2016077403 A1 * 5/2016 ............... A61L 2/10
WO 2019190967 A1 10/2019

OTHER PUBLICATIONS

Italian Search Report for IT Patent Application No. 202100004727, Nov. 25, 2021, Munich, DE, 9 pages.

* cited by examiner

*Primary Examiner* — Kevin Joyner
(74) *Attorney, Agent, or Firm* — Armstrong Teasdale LLP

(57) ABSTRACT

A method for controlling a mobile robotic apparatus for disinfecting a space includes acquiring, by a data processing unit of the mobile robotic apparatus, a map of the space to be disinfected, acquiring information on a plurality of contact surfaces to be disinfected within the space to be disinfected, each contact surface being associated with a criticality level, determining an amount of ultraviolet-C, UV-C, radiation energy to be deposited, by a UV-C radiation source, on a contact surface, the amount of UV-C radiation energy being determined as a function of the criticality level, distance and orientation of the contact surface with respect to the UV-C radiation source and of set operating features of the UV-C radiation source, determining a respective virtual potential of attraction of the UV-C radiation source towards each contact surface, generating a path trajectory, and con-
(Continued)

trolling the mobile robotic apparatus along the generated path trajectory.

11 Claims, 9 Drawing Sheets

(52) U.S. Cl.
CPC ........ *G05D 1/0274* (2013.01); *A61L 2202/11* (2013.01); *A61L 2202/14* (2013.01); *A61L 2202/16* (2013.01)

(58) Field of Classification Search
CPC ............ A61L 2202/14; A61L 2202/16; A61L 2202/25; A61L 2/26; G05D 1/0219; G05D 1/0274; G05D 1/024; G05D 1/0272; G05D 1/0276; G08C 17/02; H04Q 9/00
See application file for complete search history.

METHOD FOR CONTROLLING A MOBILE ROBOTIC APPARATUS FOR DISINFECTING A SPACE AND MOBILE ROBOTIC APPARATUS FOR DISINFECTING A SPACE IMPLEMENTING SUCH METHOD

CROSS-REFERENCE TO RELATED APPLICATION

This application claims priority to Italian Patent Application No. 102021000004727 filed on Mar. 1, 2021, the entire contents of which are hereby incorporated herein by reference.

FIELD OF THE INVENTION

The present invention relates to the field of robotics and, in particular, to a method for controlling a mobile robotic apparatus for disinfecting a space and to a mobile robotic apparatus for disinfecting a space implementing such method.

BACKGROUND OF THE INVENTION

The spread of SARS-CoV-2 virus has posed new challenges and constraints to daily life, particularly concerning safe access to public spaces, shared spaces, and workplaces.

In this regard, robotic technology, along with artificial intelligence and automation, can be used effectively to disinfect spaces, administer drugs or serve food, and perform remote diagnostics, limiting human operators' risk of exposure to potentially contaminated spaces.

As for disinfection, there are several so-called "no-touch" solutions for disinfecting spaces and surfaces, where the use of ultraviolet-C (UV-C) radiation is very effective for inactivating viruses and disinfecting bacteria on surfaces, reducing contamination on high-contact surfaces.

The evolution of robotic technology, combined with UV-C radiation systems, has led to the development of mobile robotic apparatus with UV-C radiation sources which represent a significant advantage over fixed UV-C radiation sources.

Indeed, a mobile UV-C radiation source can overcome many of the obvious limitations of a fixed UV-C radiation source which, for example, cannot provide equivalent levels of UV-C radiation doses at different distances from the source, considering that an administered dose of UV-C radiation is a function of both intensity of UV-C radiation and exposure time to UV-C radiation.

Nowadays, a need is strongly felt to control a mobile robotic apparatus for disinfecting a space with UV-C radiation to optimize as much as possible both the path to be followed within the space to be disinfected and the provision of UV-C radiation to ensure an appropriate UV-C radiation dose on each contact surface in the space.

SUMMARY OF THE INVENTION

It is an object of the present invention to devise and provide a method for controlling a mobile robotic apparatus for disinfecting a space which allows at least partially obviating the drawbacks described with reference to the prior art, and optimizing as much as possible both the path to be followed within the space to be disinfected and the provision of UV-C radiation to ensure an appropriate UV-C radiation dose on each contact surface to be disinfected within the space.

Such an object is achieved by a method as described and claimed herein.

Preferred embodiments are also described.

The present invention further relates to a mobile robotic apparatus for disinfecting a space implementing such method.

BRIEF DESCRIPTION OF THE DRAWINGS

Further features and advantages of the method and the mobile robotic apparatus according to the present invention will be apparent from the following description which illustrates preferred embodiments, given by way of indicative, non-limiting examples, with reference to the accompanying figures, in which.

It is worth noting that, in the figures, equivalent or similar elements are indicated by the same numeric and/or alphanumeric references.

DETAILED DESCRIPTION

Figure 1A:
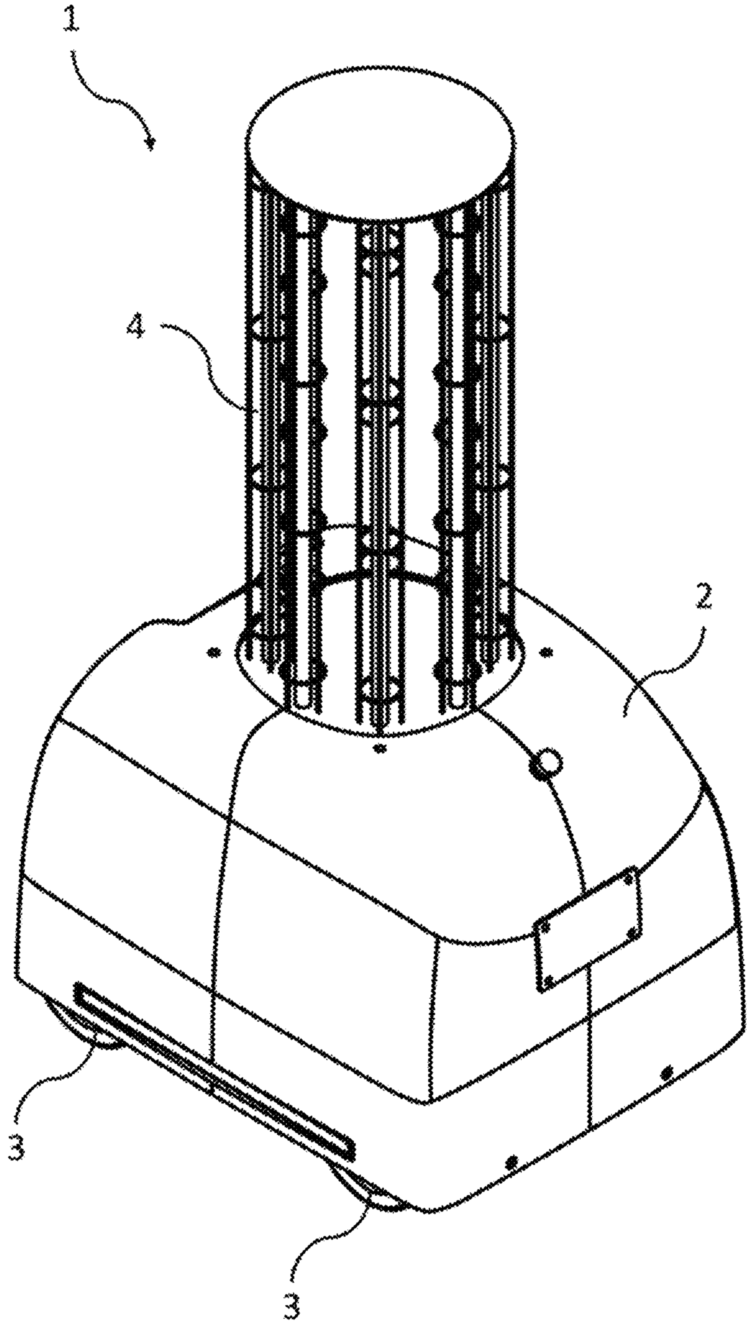
FIGS. 1*a* and 1*b* show, respectively, a perspective view from above and a side perspective view of a mobile robotic apparatus for disinfecting a space according to an embodiment of the present invention.

A mobile robotic apparatus for disinfecting a space will now be described with reference to the figures.

The mobile robotic apparatus for disinfecting a space, hereinafter also mobile robotic apparatus or simply apparatus, is indicated as a whole by reference numeral 1.

The space to be disinfected is indicated in the figures by reference numeral 100.

For the purposes of this description, "space" means any confined space, either indoors or outdoors, which requires periodical disinfection and/or after use to safeguard health and safety of users of the space.

Examples of "spaces" are meeting rooms, conference rooms, operating rooms, medical examination rooms, airport or train station lobbies, waiting rooms, rooms, bars, restaurants, classrooms, gymnasiums, and so on.

The space 100 comprises a plurality of contact surfaces to be disinfected within the space 100.

Contact surface means any surface that can be touched by a user.

Examples of contact surfaces to be disinfected are door and/or window handles, furniture knobs, the top of a table or furniture in general, comprising objects resting thereon, the back and/or arms of a chair, the legs of a table or furniture in general, a shelf, a wall, but also office equipment such as keyboards, mouse, screens, computers, and so on.

Each contact surface to be disinfected is associated with a criticality level with respect to which a related level of disinfection is to be ensured.

Each criticality level is associated with contact frequency and risk of exposure to a virus or other contaminant.

The criticality level is determined according to the type of contact surface to be disinfected.

For example, a door handle of an access door to the space, frequently in contact with the hands of the users opening and closing the door, will have a set criticality level and a corresponding level of disinfection greater than the set criticality level and the corresponding level of disinfection of a shelf inside the space, less frequently in contact with the hands of the users.

Referring back to the apparatus 1, the apparatus 1 comprises a mobile base 2 comprising a plurality of wheels 3, preferably omnidirectional wheels.

The apparatus 1 further comprises at least one UV-C radiation source 4 mounted on the mobile base 2.

Figure 1B:
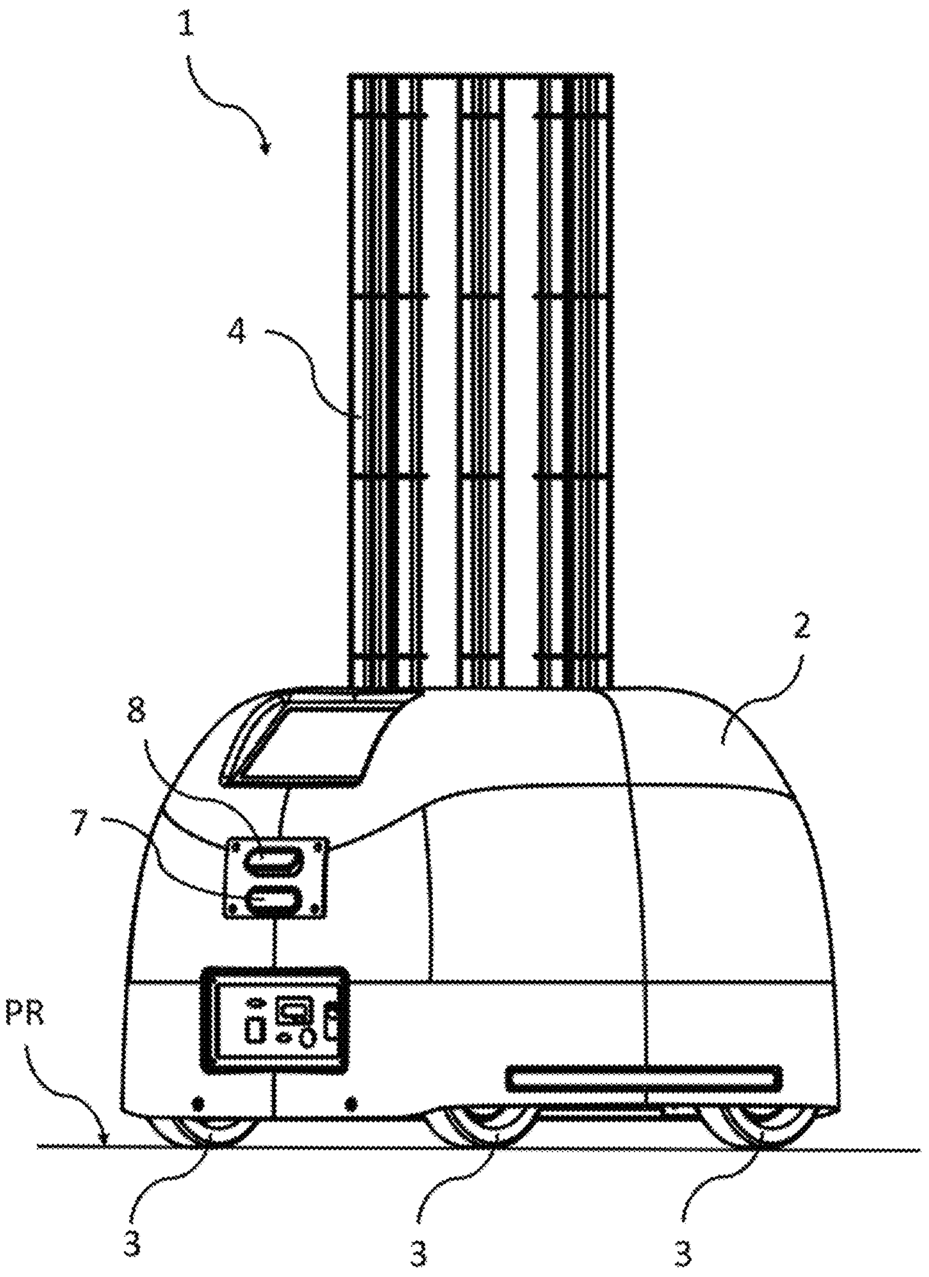
Figure 2:
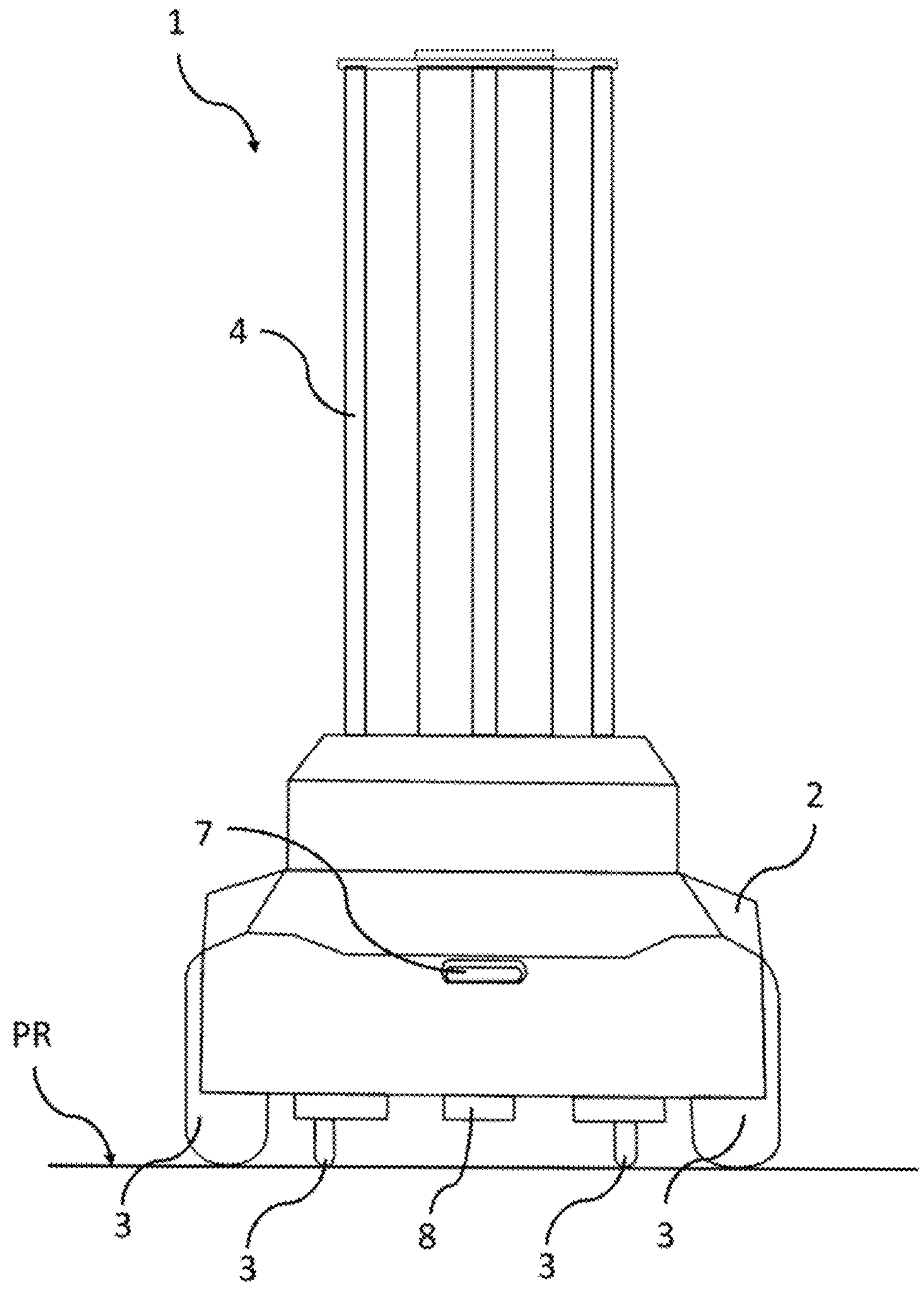
FIG. 2 shows a front view of a mobile robotic apparatus for disinfecting a space according to a further embodiment of the present invention.

According to an embodiment shown in FIGS. 1*a*, 1*b* and 2, the at least one UV-C radiation source 4 comprises a plurality of UV-C radiation lamps.

In greater detail, each UV-C radiation lamp has a tubular shape and extends vertically from the mobile base 2 along a direction substantially orthogonal to a reference plane PR, i.e., a plane of motion on which the apparatus 1 can move (diagrammatically shown in FIGS. 1*b* and 2).

The plurality of UV-C radiation lamps is mounted on the mobile base 2 at installation points distributed on the mobile base 2, such as in the center, along a circumference, and preferably equidistant from each other.

Figure 3:
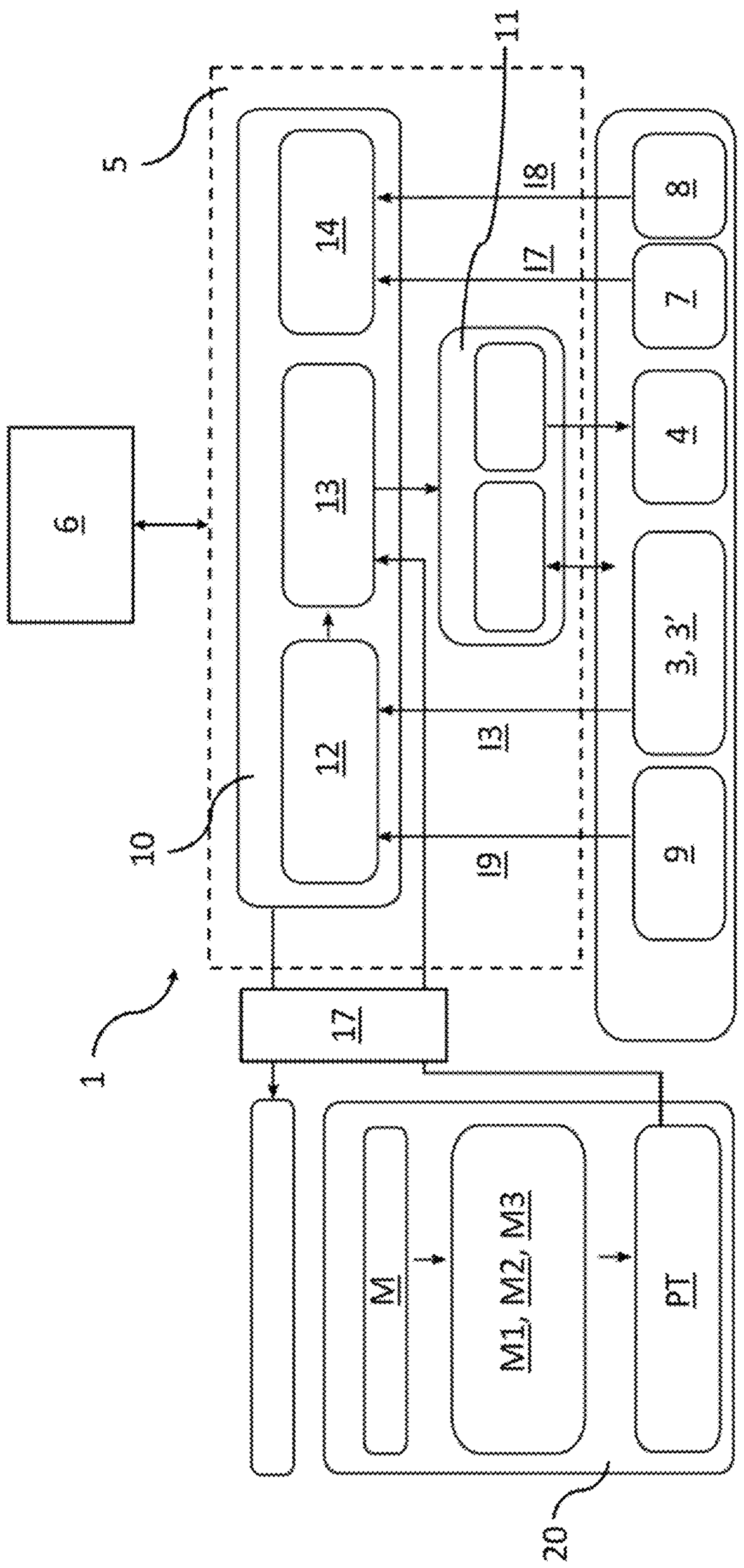
FIG. 3 shows, by means of a block chart, an architecture for controlling a mobile robotic apparatus for disinfecting a space according to an embodiment of the present invention.

The apparatus 1, in general, further comprises a data processing unit 5, shown in FIG. 3, operatively connected to the at least one UV-C radiation source 4.

The data processing unit 5 is integrated into the mobile base 2.

The data processing unit 5 is, for example, one or more microcontrollers or microprocessors.

From a functional point of view, as will be described with particular reference to the architecture in FIG. 3, the data processing unit 5 comprises hardware modules appropriately configured from a software point of view and/or software logic for controlling operation of the apparatus 1.

The apparatus 1 further comprises a memory unit 6 operatively connected to the data processing unit 5.

The memory unit 6, also integrated into mobile base 2, can be either internal or external (e.g., as shown in FIG. 3) to the data processing unit 5.

It is worth noting that the memory unit 6 is configured to store one or more program codes which are executable by the data processing unit 5 and data generated and processed following the execution of one or more program codes by the data processing unit 5.

In this regard, as will also be reiterated below, the data processing unit 5 is configured to perform a method for controlling the apparatus 1, described later with particular reference also to FIG. 6.

The apparatus 1 further comprises at least one first artificial vision sensor 7 operatively connected to the data processing unit 5.

The at least one first artificial vision sensor 7 is configured to provide the data processing unit 5 with first information 17 representative of a geometry of the space 100 explored by the apparatus 1.

Examples of first information 17 are RGB images and point clouds (RGB+Depth) related to the explored space.

The at least one first artificial vision sensor 7 is preferably positioned at the front of the mobile base 2, as shown for example in FIGS. 1*b* and 2.

Examples of the at least one first artificial vision sensor 7 are a three-dimensional depth camera, light detection and ranging (LIDAR) sensors, ultrasonic sensors, sensorized mechanical buffers, and in general any sensor which allows acquiring data about the positioning of a point in the space with respect to the mobile robotic apparatus, which can be used either together or individually.

According to a further embodiment, in combination with the preceding embodiment, the apparatus 1 further comprises at least one second artificial vision sensor 8 configured to provide the data processing unit 5 with second information 18 representative of the space 100 explored by the apparatus 1.

Examples of second information 18 are RGB images and point clouds (RGB+Depth) related to the explored space.

The at least one second artificial vision sensor 8 is preferably positioned at the front of the mobile base 2, as shown for example in FIG. 2.

Examples of the second artificial vision sensor is a depth detection (LI DAR) module configured to determine the distance of an object (obstacle) or a surface from the apparatus 1, a three-dimensional depth camera, ultrasonic sensors, sensorized mechanical buffers, and generally any sensor which allows acquiring data about the positioning of a point in the space with respect to the mobile robotic apparatus, which may be used either together or individually.

The apparatus 1 further comprises at least one inertial measurement unit (IMU) 9, operatively connected to the data processing unit 5.

The at least one IMU 9, integrated into the mobile base 2, is configured to provide the data processing unit 5 with information 19 representative of dynamics (e.g., linear accelerations, velocities and angular accelerations, orientation of the earth's magnetic field with respect to the sensor, and orientation of gravity with respect to the sensor) of the apparatus 1 during movement.

The IMU 9 may be a multiple sensor including at least one accelerometer, at least one magnetometer, and at least one gyroscope, which allow extracting information representative of the above listed dynamics of the apparatus 1 during movement.

The apparatus 1 further comprises a plurality of odometer sensors 3' configured to provide the data processing unit 5 with information 13 representative of a displacement of the apparatus 1 within the space 100.

Each of the odometer sensors of the plurality of odometer sensors 3' is operatively connected to a respective wheel of the plurality of wheels 3.

Each odometer sensor 3' may be an angular position transducer (encoder) configured to provide an information 13 representative of an angular displacement of the respective wheel 3 to which the odometer sensor is operatively connected.

With particular reference to FIG. 3, it should be noted that, from a functional point of view, the data processing unit 5 comprises a first control module 10 and a second control module 11.

The first control module 10 may be referred to as a high-level controller of the apparatus 1 while the second control module 11 may be referred to as a low-level controller of the apparatus 1.

The first control module 10 comprises an odometer module 12 configured to determine the position of the mobile apparatus 1 in the space 100 based on the information 19 representative of the dynamics of the apparatus 1 during movement provided by the at least one IMU 9 and the information 13 representative of a displacement of the apparatus 1 within the space 100 provided by the plurality of odometer sensors 3'.

The first control module 10 further comprises a position and orientation control module 13 of the apparatus 1 configured to determine control signals SC to be provided to the apparatus 1 based on the position of the mobile apparatus 1 in the space 100 determined by the odometer module 11 and an optimized reference path trajectory PT provided by a remote computer 20, described in greater detail hereinafter.

The first control module 10 further comprises a simultaneous localization and mapping (SLAM) module 14 configured to determine the localization of the apparatus 1 and the simultaneous mapping of the space 100 in which the apparatus 1 is located, based on the first information 17 representative of a geometry of the space 100 explorable by the apparatus 1 and the second information 18 representative of a geometry of the space 100 explorable by the apparatus 1 provided by the at least one first artificial vision sensor 7 and the at least one second artificial vision sensor 8, respectively.

The localization of the apparatus 1 and the simultaneous mapping of the space 100 within which the apparatus 1 is located are both used in real-time for navigation control of the apparatus 1.

Furthermore, as will be reiterated below, the simultaneous mapping of the space 100 in which the apparatus 1 is located, once acquired, is also used as input into a trajectory optimization algorithm, which allows to generate the optimal sanitization trajectories.

The second control module 11 comprises a wheel speed control module 15 configured to control the plurality of omnidirectional wheels 3 of the apparatus 1 based on the control signals SC provided by the position and orientation control module 13 of the apparatus 1 and based on the information 13 representative of a displacement of the robotic apparatus 1 within the space 100 provided by the plurality of odometer sensors 3'.

Examples of control signals SC that may be sent to the wheel speed control module 15 are linear and/or angular velocity references, or position and/or orientation references.

The second control module 11 further comprises a UV-C radiation source control module 16 configured to control the at least one UV-C radiation source 4 based on the control signals SC provided by the position and orientation control module 13 of the apparatus 1.

A control signal SC which may be sent to the UV-C radiation source control module 16 is, for example, an on/off digital signal.

Referring again to FIG. 3, according to a further embodiment, the apparatus 1 comprises a data communication module 17 operatively connected to the data processing unit 5.

The data communication module 17 is configured to be operatively connected to the remote computer 20, previously introduced, through a data communication network (not shown in the figures).

The remote computer 20, e.g., an electronic calculator or a personal computer, is configured to remotely control the operation of the mobile apparatus 1.

In greater detail, the remote computer 20 is configured to receive information 15 representative of the operation of the apparatus 1 from the data processing unit 5.

In this manner, by means of the remote computer 20, it is possible for a user, to remotely supervise the behavior of the apparatus 1, in total safety with respect to the space 100 to be disinfected in which the apparatus 1 is located.

The remote computer 20 is also configured to perform an offline optimization of the control of the apparatus 1.

In greater detail, the remote computer 20 is configured to determine an optimized reference path trajectory PT from a static map M of the space 100 to be disinfected, employing a trajectory generation and movement planning algorithm specific to disinfection procedures based on the following three modules:

a first module M1 of artificial potential field (APF) configured to determine the speed of the apparatus 1 and guide the apparatus 1 along the contact surfaces to be disinfected based on the distance therefrom and the amount of energy stored by the surfaces;

a second module M2 of physical simulation of the radiation physics and the movement of the apparatus 1 in the space 100 configured to modulate over time the APF value and the amount of energy released on the surfaces; and a third module M3 of automatic optimization configured to optimize the process based on a genetic algorithm (GA).

The remote computer 20 is also configured to provide the optimized reference path trajectory PT determined to the data processing unit 5 of the apparatus 1.

Returning generally to the mobile robotic apparatus 1, according to the present invention, the data processing unit 5 of the apparatus 1 is configured to acquire a map M of a space 100 to be disinfected.

Furthermore, the data processing unit 5 of the apparatus 1 is configured to acquire information of a plurality of contact surfaces to be disinfected present within the space 100 to be disinfected.

As mentioned hereinabove, each contact surface is associated with a set criticality level with respect to which a related level of disinfection is to be ensured.

The data processing unit 5 of the apparatus 1 is configured to determine an amount of UV-C radiation energy to be deposited, through the at least one UV-C radiation source 4 mounted on the mobile base 2 of the apparatus 1, on a respective contact surface of the plurality of contact surfaces to be disinfected.

The data processing unit 5 of the apparatus 1 is configured to determine the amount of UV-C radiation energy as a function of the criticality level of the contact surface to be disinfected, of the distance and the orientation of the contact surface to be disinfected with respect to the at least one UV-C radiation source 4, and of set operating features of the at least one UV-C radiation source 4.

The set operating features of the at least one UV-C radiation source 4 comprise: surface, geometric arrangement, shape, and radiation power.

In order to determine the amount of UV-C radiation energy, the data processing unit 5 of the apparatus 1 is configured to implement a respective physical model of light radiation which can be represented by the following mathematical relationship (1):

$$I(\vec{r},\hat{n}) = \frac{P}{4\pi A}\oint\!\!\oint_A \frac{\eta(\vec{r},\hat{n})}{|\vec{r}|^2}dA \quad (1)$$

where:

I=intensity (amount) of light radiation;

r=distance of the at least one UV-C radiation source 4 from the contact surface to be disinfected;

A=area of at least one UV-C radiation source 4;

n=normal of the contact surface to be disinfected;

η=optical efficiency value, which can be determined using the following mathematical relationship (2):

$$\eta(\vec{r},\hat{n}) = \begin{cases} \frac{|\vec{r}\cdot\hat{n}|}{|\vec{r}|} & \vec{r}\cdot\hat{n} \le 0 \\ 0 & \vec{r}\cdot\hat{n} > 0 \end{cases} \quad (2)$$

Furthermore, the data processing unit 5 of the apparatus 1 is configured to determine, for each time instant $t_i$, 1<i<N, of a plurality of time instants, a respective virtual potential of attraction of the UV-C radiation source 4 towards each contact surface to be disinfected of the plurality of contact surfaces to be disinfected, by modulating over time the virtual attraction potential of the at least one UV-C radiation source 4 towards each contact surface of the plurality of contact surfaces to be disinfected as a function of the amount of radiation energy determined for each contact surface to be disinfected and radiated at the previous time instant $t_{i-1}$.

The virtual (or artificial) potential is a value of energy level determinable by means of a mathematical model representative of a law of attraction or repulsion towards each contact surface to be disinfected of the plurality of contact surfaces to be disinfected.

The virtual (or artificial) potential can be determined, as an example, by implementing the following mathematical relationship (3):

$$U(\vec{r_i},t) = -k + \sum_i w_i(t)\frac{1}{|\vec{r_i}|^n} \quad (3)$$

where:

U=virtual (or artificial) potential;

k=constant of determination of an intensity of the virtual potential;

n=exponent of determination of a change in the virtual potential as a function of the distance of the at least one UV-C radiation source 4 from a contact surface to be disinfected;

$w_i$=weight of the contact surface to be disinfected determinable by the following mathematical relationship (4):

$$w_i(t) = \begin{cases} 1 + mf(\lambda_i) & \lambda_i < 1 \\ 0 & \lambda_i \ge 1 \end{cases} \quad (4)$$

where:

$E_0$=radiation energy density to be achieved to have a level of disinfection such that a specific virus or bacterium is inactivated;

$E_1$=energy stored by the same contact surface to be disinfected in the previous transit of the apparatus 1;

$$\lambda_i = \frac{E_i(t)}{E_0}$$

variable function of the energies $E_1$ and $E_0$;

$f(\lambda_i)$ is a function of $\lambda_i$ defined positive i.e., such that $f(\lambda_i) \ge 0$ valid for every $\lambda_i \ge 0$ m=coefficient representing the maximum possible limit of the weight of the contact surface to be disinfected.

Therefore, the determined virtual potential of attraction of the at least one UV-C radiation source 4 towards a contact surface to be disinfected is function of both the radiation energy density to be achieved to have a level of disinfection such that a specific virus or bacterium is inactivated and the energy stored by the same contact surface to be disinfected in the previous transit of the apparatus 1.

The data processing unit 5 of the apparatus 1 is also configured to generate a path trajectory as a function of each determined virtual potential of attraction of the at least one radiation source 4 towards each contact surface to be disinfected.

It is worth noting that the sum of all potential contributions is a potential function which is then used to obtain by mathematical calculations a speed or acceleration to be given to the apparatus 1, either in real-time or in simulation.

Therefore, the path trajectory is generated as directional speed or acceleration to be provided to the apparatus 1, either in real-time or in simulation, on the basis of each determined virtual potential of attraction of the at least one UV-C radiation source 4 towards each contact surface to be disinfected, i.e. also of the energy stored by each contact surface to be disinfected in the previous transit of the apparatus 1.

In greater detail, the path trajectory (directional speed) is generated as gradient of the determined virtual potential of attraction of the at least one UV-C radiation source 4 towards each contact surface to be disinfected.

Finally, the data processing unit 5 is configured to control the apparatus 1 within the space 100 to be disinfected along the generated path trajectory.

According to an embodiment, in combination with the preceding one, the data processing unit 5 of the apparatus 1 is configured to generate the path trajectory based on a gradient of the determined virtual potential of attraction of the at least one UV-C radiation source 4 towards each contact surface to be disinfected to obtain a sliding of the mobile robotic apparatus 1 along obstacles encountered within the space to be disinfected along the path trajectory taken.

The gradient of the determined virtual potential can be expressed by the following mathematical relationship (5):

$$\vec{v} = \sum_i -\nabla U_i = \sum_i knw_i(t)\frac{\vec{r_i}}{|\vec{r_i}|^{-(n+2)}} \quad (5)$$

According to a further embodiment, in combination with any one of those described above, the data processing unit 5 of the apparatus 1 is configured to perform an optimization procedure of a plurality of parameters employed to determine a respective virtual potential of attraction of the at least one radiation source towards each contact surface to be disinfected of the plurality of contact surfaces to be disinfected, based on different values of virtual potential of attraction of the at least one radiation source towards each contact surface of said plurality of contact surfaces.

The optimized parameters introduced above with the references k, n, and m in the mathematical relationships (3) and (4) are representative of path trajectories capable of ensuring that the mobile robotic apparatus travels in a set minimum time through the space to be disinfected providing an appropriate radiation dose on each contact surface to be disinfected, i.e., travels an optimal sanitization trajectory.

As mentioned above, the optimization procedure may also employ as input the simultaneous mapping of the space 100 within which the apparatus 1 is located, once acquired.

According to an embodiment, in combination with any one of those described above, the acquisition of a map of a space 100 to be disinfected can be directly performed by the data processing unit 5 of the apparatus 1 or provided by the remote computer 20 with respect to the apparatus 1 and in communication therewith through the data communication network.

According to an embodiment, alternative to the preceding one, the acquisition of information of a plurality of contact surfaces to be disinfected can be performed by the data processing unit 5 of the apparatus 1 or provided by the remote computer 20 with respect to the apparatus 1 and in communication therewith through the data communication network.

Figure 6:
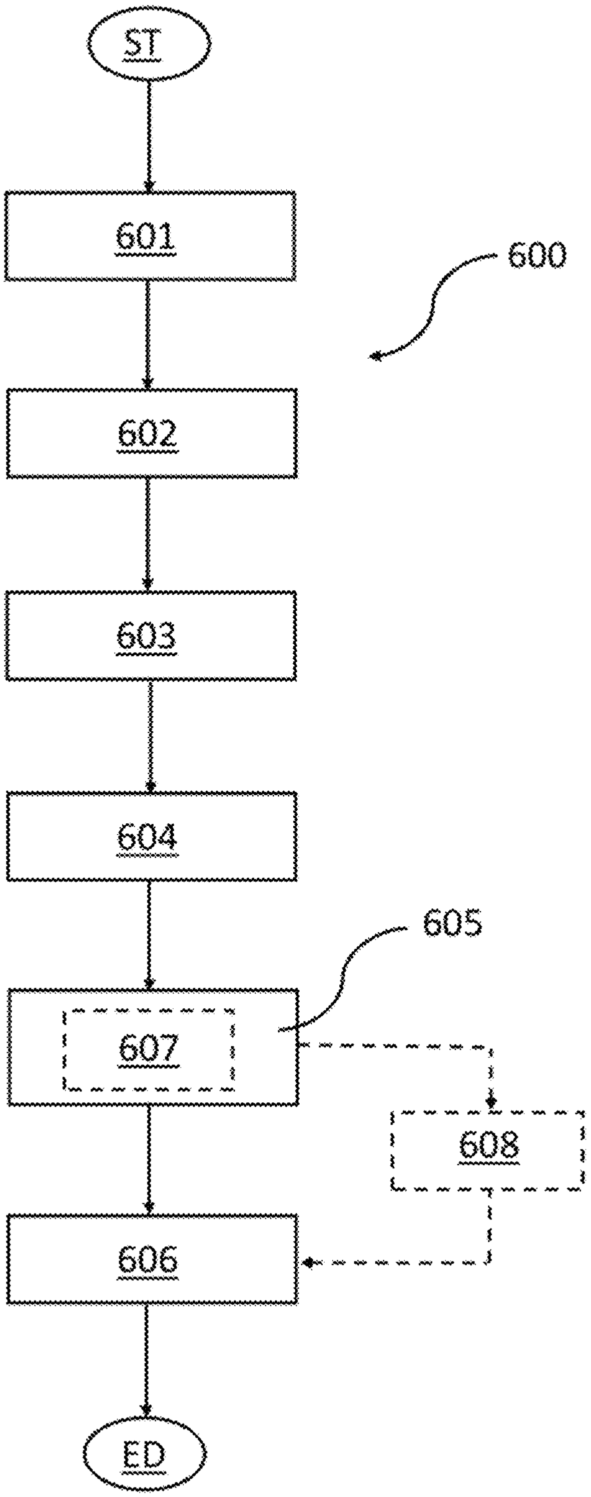
FIG. 6 shows, by means of a block chart, a method for controlling a mobile robotic apparatus for disinfecting a space, according to an embodiment of the present invention.

With reference now also to FIG. 6, a method 600 for controlling a mobile robotic apparatus 1 for disinfecting a space 100, hereinafter also only method for controlling or simply method, according to the present invention, will be described.

It is worth noting that the components of apparatus 1 and the information previously described with reference to the apparatus 1 that will also be mentioned with reference to the method 600 will not be repeated in detail for the sake of brevity.

The method 600 comprises a symbolic step of starting ST.

The method 600 comprises a step a) of acquiring 601, by the data processing unit 5 of the mobile robotic apparatus 1, a map M of a space 100 to be disinfected.

The method 600 further comprises a step of b) acquiring 602, by the data processing unit 5 of the mobile robotic apparatus 1, information about a plurality of contact surfaces to be disinfected within the space 100 to be disinfected.

Each contact surface to be disinfected is associated with a criticality level with respect to which a related level of disinfection is to be ensured.

The criticality level and the related level have been defined above.

Examples of space 100 and contact surfaces to be disinfected have been provided above.

The method 600 further comprises a step of c) determining 603, by the data processing unit 5 of the mobile robotic apparatus 1, an amount of UV-C radiation energy to be deposited, by at least one UV-C radiation source 4 mounted on the mobile robotic apparatus 1, on a respective contact surface of the plurality of contact surfaces to be disinfected.

The amount of UV-C radiation energy is determined as a function of the criticality level of the contact surface, of the distance and the orientation of the contact surface to be disinfected with respect to the at least one UV-C radiation source 4, of set operating features of the at least one UV-C radiation source 4.

The set operating features of the at least one radiation source 4 comprise: surface, geometric arrangement, shape, and radiation power.

The physical radiation model used to determine the amount of UV-C radiation energy was described above.

Again with reference to FIG. 6, the method 600 further comprises a step of d) determining 604, for each time instant $t_i$, 1<i<N, of a plurality of time instants, by the data processing unit 5 of the mobile robotic apparatus 1, a respective virtual potential of attraction of the at least one UV-C radiation source 4 towards each contact surface of the plurality of contact surfaces, by modulating over time the virtual potential of attraction of the at least one UV-C radiation source 4 towards each contact surface to be disinfected of the plurality of contact surfaces as a function of the amount of radiation energy determined for each contact surface to be disinfected and radiated at the previous time instant $t_{i-1}$.

As previously described, the virtual (or artificial) potential is a value of energy level determinable by a mathematical model representative of a law of attraction or repulsion towards each contact surface to be disinfected of the plurality of contact surfaces to be disinfected.

The determined virtual potential of attraction of the at least one UV-C radiation source 4 towards a contact surface to be disinfected is function of both the radiation energy density to be achieved to have a level of disinfection such that a specific virus or bacterium is inactivated and the energy stored by the same contact surface to be disinfected in the previous transit of the apparatus 1.

The mathematical relationships underlying the determination of the virtual potential have been described above.

The method 600 further comprises a step e) of generating 605, by the data processing unit 5 of the mobile robotic apparatus 1, a path trajectory TP as a function of each determined virtual potential of attraction of the at least one UV-C radiation source 4 towards each contact surface to be disinfected.

Figure 4B:
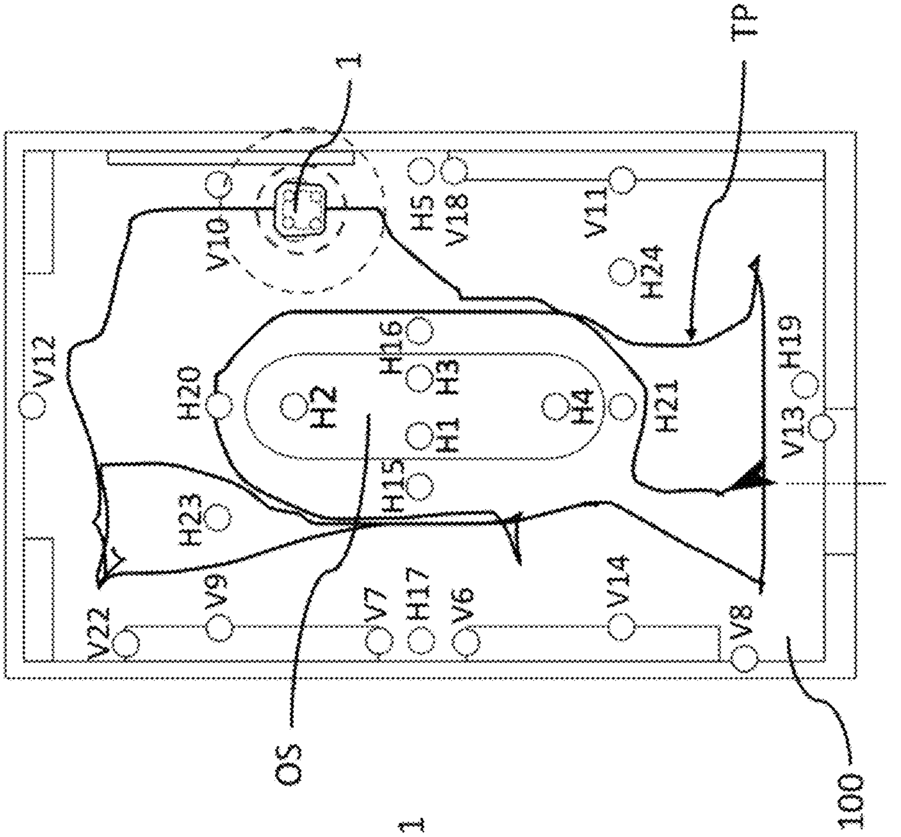
FIG. 4*b* diagrammatically shows the space in FIG. 4*a* in which it is represented a further example of a path trajectory which can be traveled through by a mobile robotic apparatus for disinfecting a space according to the present invention.
Figure 4A:
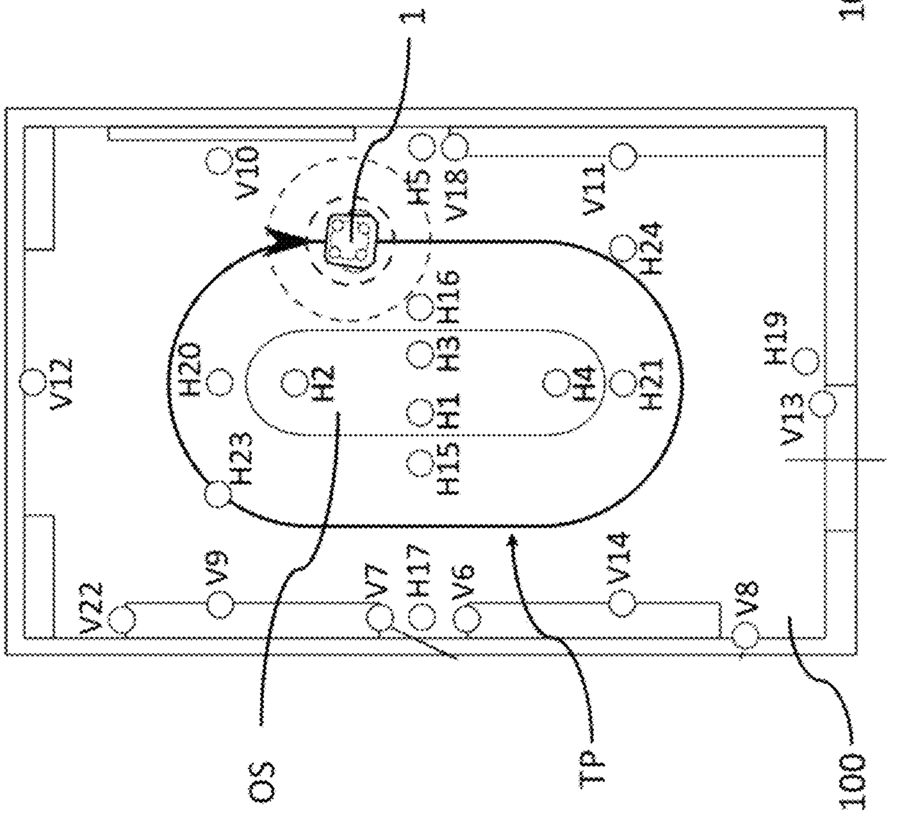
FIG. 4*a* diagrammatically shows a space in which it is represented an example of a path trajectory which can be traveled through by a mobile robotic apparatus for disinfecting a space according to the present invention.
Figure 5B:
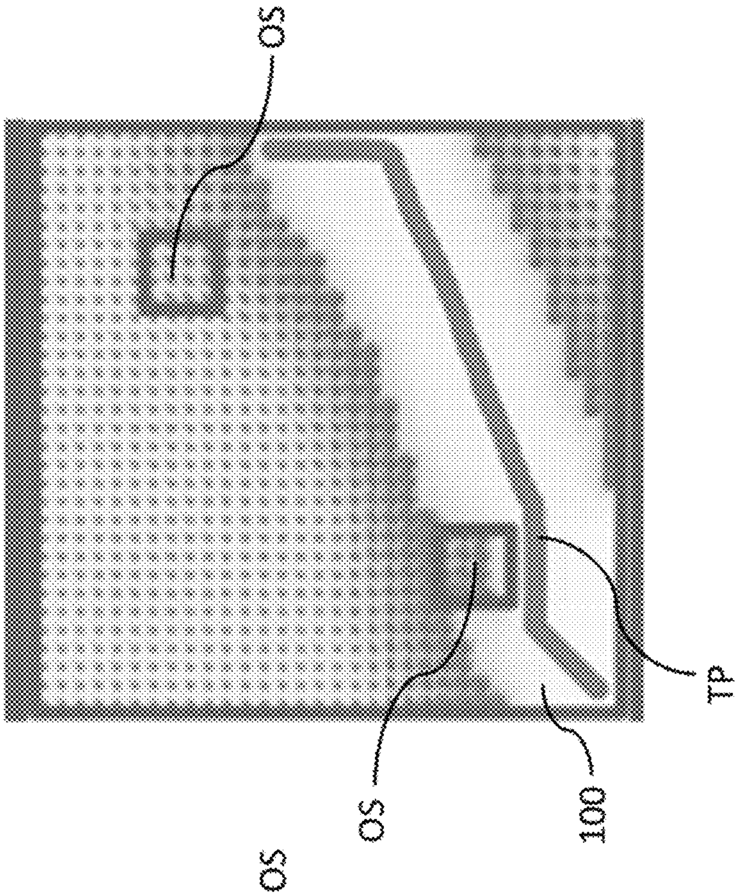
FIGS. 5*a*-5*f* diagrammatically show a space in which it is represented in successive instants of time a further example of a path trajectory which can be traveled through by a mobile robotic apparatus for disinfecting a space according to the present invention.
Figure 5A:
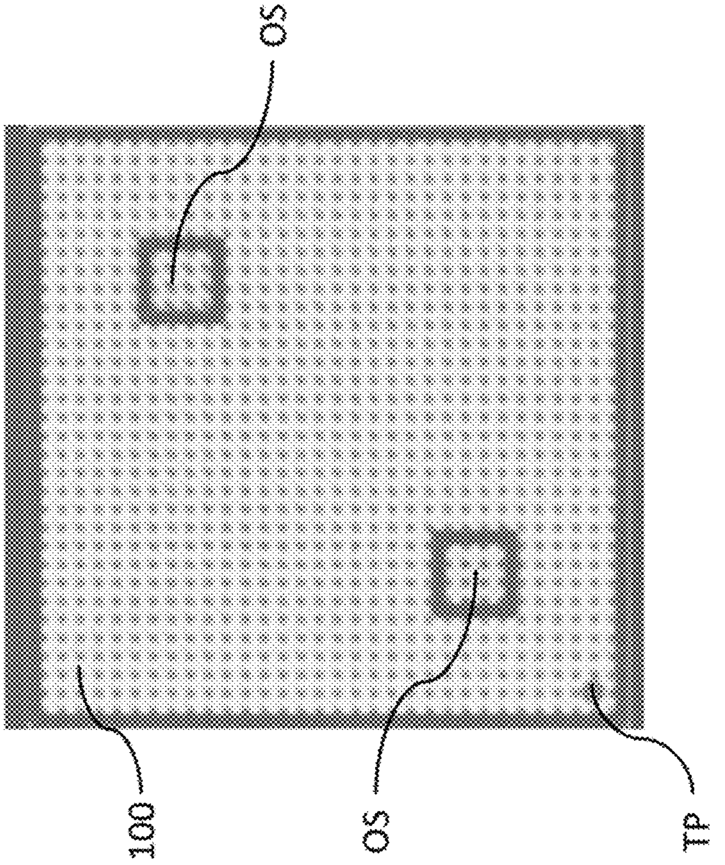
Figure 5C:
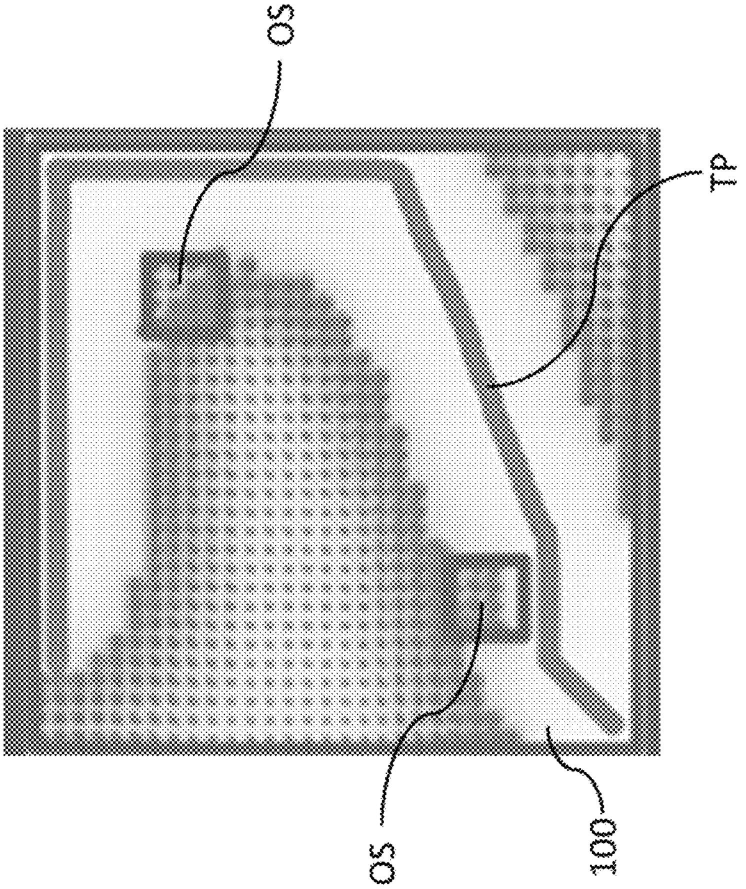
Figure 5D:
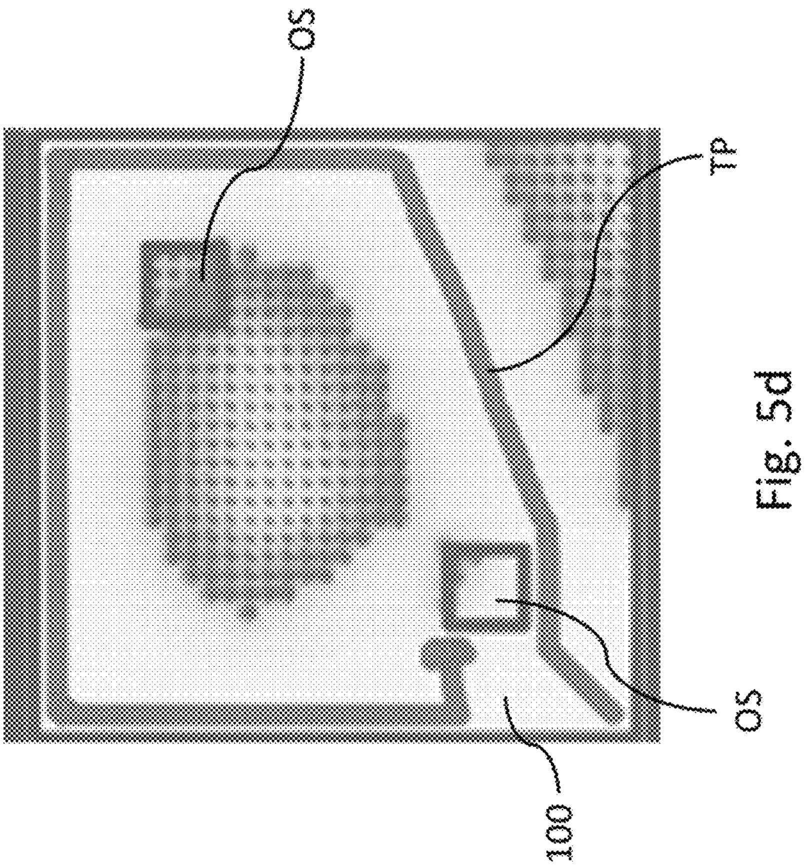
Figure 5F:
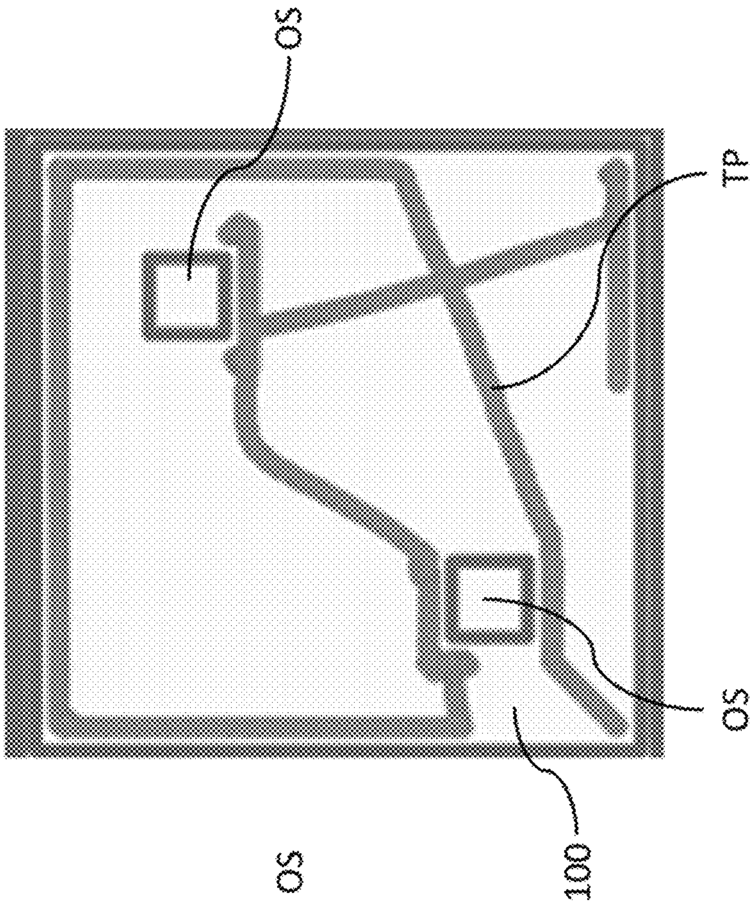
Figure 5E:
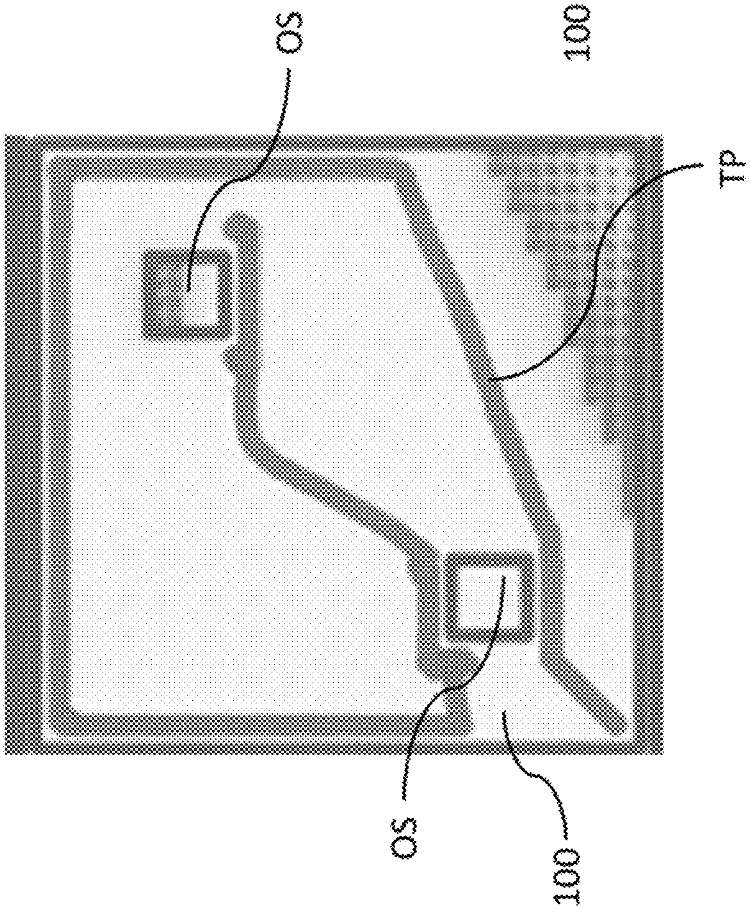

FIGS. 4*a* and 4*b* show a generated path trajectory TP which can be traveled by an apparatus 1 within a space 100 to be disinfected.

As previously described, the path trajectory is therefore generated as directional speed or acceleration to be provided to the apparatus 1, either in real-time or in simulation, on the basis of each determined virtual potential of attraction of the at least one UV-C radiation source 4 towards each contact surface to be disinfected, i.e. also of the energy stored by each contact surface to be disinfected in the previous transit of the mobile robotic apparatus 1.

In greater detail, the path trajectory (directional speed) is generated as gradient of the determined virtual potential of attraction of the at least one UV-C radiation source 4 towards each contact surface to be disinfected.

The method 600 further comprises a step f) of controlling 606, by the data processing unit 5 of the mobile robotic apparatus 1, the mobile robotic apparatus 1 along the generated path trajectory (FIGS. 4*a* and 4*b*).

The method 600 comprises a symbolic step of ending ED.

According to an embodiment, in combination with the preceding one and shown with dashed lines in FIG. 6, the step of e) generating 605 further comprises a step of g) generating 607 the path trajectory based on a gradient of the determined virtual potential of attraction of the at least one UV-C radiation source 4 towards each contact surface to be disinfected to achieve a sliding of the mobile robotic apparatus 1 along obstacles encountered within the space to be disinfected along the traveled path trajectory.

Examples of obstacles are shown in FIGS. 4*a*, 4*b*, and 5*a*-5*f*, indicated by reference OS.

According to an embodiment, in combination with any one of those described above, the method 600 further comprises a step of h) performing 608 a procedure for optimizing a plurality of parameters employed to determine respective virtual potential of attraction of the at least one UV-C radiation source 4 towards each contact surface to be disinfected of the plurality of contact surfaces to be disinfected, based on different values of virtual potential of attraction of the at least one UV-C radiation source 4 towards each contact surface to be disinfected of the plurality of contact surfaces to be disinfected.

The optimized parameters introduced above with the references k, n, and m in the mathematical relations (3) and (4) are representative of optimized path trajectories capable of ensuring that the mobile robotic apparatus 1 travels in a set minimum time through the space 100 to be disinfected while providing an appropriate radiation dose for disinfection on each contact surface to be disinfected.

FIG. 4*b* shows an optimized path trajectory TP which can be traveled by an apparatus 1 within a space 100 to be disinfected.

According to an embodiment, in combination with any one of those previously described, step a) may be directly performed by the data processing unit 5 of the mobile robotic apparatus 1 or may be provided by a remote computer 20 with respect to the mobile robotic apparatus 1 and in communication therewith by a data communication network.

According to an embodiment, in combination with any one of those previously described, step b) may be directly performed by the data processing unit 5 of the mobile robotic apparatus 1 or may be provided by a remote computer 20 with respect to the mobile robotic apparatus 1 and communication therewith by a data communication network.

An example of operation of the mobile robotic apparatus 1 for disinfecting a space 100 to be disinfected will be described now with reference to the figures.

A data processing unit 5 of a mobile robotic apparatus 1 acquires a map M of a space 100 to be disinfected.

The data processing unit 5 of the mobile robotic apparatus 1 acquires information of a plurality of contact surfaces to be disinfected present within the space 100 to be disinfected.

Each contact surface to be disinfected is associated with a criticality level with respect to which a related level of disinfection is to be ensured.

The data processing unit 5 of the mobile robotic apparatus 1 determines an amount of UV-C radiation energy to be deposited, by at least one UV-C radiation source 4 mounted on the mobile robotic apparatus 1, on a respective contact surface to be disinfected of the plurality of contact surfaces to be disinfected.

The amount of UV-C radiation energy is determined as a function of the criticality level of the contact surface, of the distance and the orientation of the contact surface to be disinfected with respect to the at least one UV-C radiation source 4, of set operating features of the at least one UV-C radiation source 4.

The data processing unit 5 of the mobile robotic apparatus 1 determines, for each time instant $t_i$, $1<i<N$, of a plurality of time instants, a respective virtual potential of attraction of the at least one UV-C radiation source 4 towards each contact surface to be disinfected of said plurality of contact surfaces to be disinfected, by modulating over time the virtual potential of attraction of the at least one UV-C radiation source 4 towards each contact surface of said plurality of contact surfaces to be disinfected as a function of the amount of radiation energy determined for each contact surface to be disinfected and radiated at the previous time instant $t_{i-1}$.

The data processing unit 5 of the mobile robotic apparatus 1 generates a path trajectory TP as a function of each determined virtual potential of attraction of the at least one UV-C radiation source 4 towards each contact surface to be disinfected.

The data processing unit 5 of the mobile robotic apparatus 1 controls the mobile robotic apparatus 1 along the generated path trajectory TP.

As shown, the purpose of the present invention is fully achieved because the method and the mobile robotic apparatus have several advantages.

Indeed, the method according to the present invention allows obtaining a trajectory planning by employing a genetic algorithm which explores possible trajectories and disinfection outcomes of a mobile robotic apparatus moving in a tunable virtual (artificial) potential field and which is capable of maximizing the UV-C radiation dose delivered based on spatial geometry.

In particular, by comparing a conventional trajectory with an optimized trajectory, the method according to the present invention achieves better performance in terms of both coverage of radiated energy in the space and time required to complete the disinfection operation.

Furthermore, the fact that the method according to the present invention is based on an attractive potential field and on an iterative simulation based on radiation physics and optimization by genetic algorithm allows finding the most adaptive path trajectory to ensure completion of disinfection.

Furthermore, the fact that the method according to the present invention is able to simulate the path trajectory and the amount of UV-C radiation energy to be deposited, then stored in the previous transits of the apparatus, on the basis of the geometry of the space, advantageously allows to avoid a displacement within the space of sensors for detecting the deposited UV-C radiation.

Finally, the fact of being able to control the mobile robotic apparatus remotely, through the remote computer placed, for example, outside the space to be disinfected, advantageously allows increasing the safety of the user responsible of the supervision of disinfection operations.

Those skilled in the art may make changes and adaptations to the embodiments of the method and mobile robotic apparatus described above or can replace elements with others which are functionally equivalent in order to meet contingent needs without departing from the scope of protection as described and claimed herein. All the features described above as belonging to a possible embodiment may be implemented irrespective of the other embodiments described.

What is claimed is:

1. A method for controlling a mobile robotic apparatus for disinfecting a space, the method comprising steps of:

a) acquiring, by a data processing unit of the mobile robotic apparatus, a map of the space to be disinfected;

b) acquiring, by the data processing unit of the mobile robotic apparatus, information on a plurality of contact surfaces to be disinfected within the space to be disinfected, each contact surface to be disinfected being associated with a criticality level with respect to which a related level of disinfection is to be ensured;

c) determining, by the data processing unit of the mobile robotic apparatus, an amount of ultraviolet-C (UV-C) radiation energy to be deposited, by at least one UV-C radiation source mounted on the mobile robotic apparatus, on a respective contact surface to be disinfected of said plurality of contact surfaces to be disinfected, said amount of UV-C radiation energy being determined as a function of the criticality level of the contact surface to be disinfected, of distance and orientation of the contact surface to be disinfected with respect to the at least one UV-C radiation source, and of set operating features of the at least one UV-C radiation source;

d) determining, for each time instant of a plurality of time instants, by the data processing unit of the mobile robotic apparatus, a respective virtual potential of attraction of the at least one UV-C radiation source towards each contact surface to be disinfected of said plurality of contact surfaces to be disinfected, by modulating over time the virtual potential of attraction of the at least one UV-C radiation source towards each contact surface to be disinfected of said plurality of contact surfaces to be disinfected as a function of the determined amount of UV-C radiation energy for each contact surface to be disinfected and radiated at a previous time instant, said virtual potential of attraction being a value of energy level determinable by a mathematical model representative of a law of attraction or repulsion towards each contact surface to be disinfected of said plurality of contact surfaces to be disinfected;

e) generating, by the data processing unit of the mobile robotic apparatus, a path trajectory as a function of each determined virtual potential of attraction of the at least one UV-C radiation source towards each contact surface to be disinfected, the path trajectory being generated as directional speed or acceleration to be provided to the mobile robotic apparatus on the basis of each determined virtual potential of attraction of the at least one UV-C radiation source towards each contact surface to be disinfected, also comprising the energy stored by each contact surface to be disinfected in the previous transit of the mobile robotic apparatus; and f) controlling, by the data processing unit of the mobile robotic apparatus, the mobile robotic apparatus along the generated path trajectory.

2. The method of claim 1, wherein step e) further comprises a step of:

g) generating the path trajectory based on a gradient of the determined virtual potential of attraction of the at least one UV-C radiation source towards each contact surface to be disinfected to obtain a sliding of the mobile robotic apparatus along obstacles encountered within the space to be disinfected along the path trajectory taken.

3. The method of claim 2, further comprising a step of:

h) performing a procedure for optimizing a plurality of parameters used to determine the respective virtual potential of attraction of the at least one UV-C radiation source towards each contact surface to be disinfected of said plurality of contact surfaces to be disinfected, based on different values of virtual potential of attraction of the at least one UV-C radiation source towards each contact surface to be disinfected of said plurality of contact surfaces to be disinfected, said optimized parameters being representative of path trajectories capable of ensuring that the mobile robotic apparatus travels through the space to be disinfected in a set minimum time, providing an appropriate radiation dose on each contact surface to be disinfected.

4. The method of claim 1, further comprising a step of:

h) performing a procedure for optimizing a plurality of parameters used to determine the respective virtual potential of attraction of the at least one UV-C radiation source towards each contact surface to be disinfected of said plurality of contact surfaces to be disinfected, based on different values of virtual potential of attraction of the at least one UV-C radiation source towards each contact surface to be disinfected of said plurality of contact surfaces to be disinfected, said optimized parameters being representative of path trajectories capable of ensuring that the mobile robotic apparatus travels through the space to be disinfected in a set minimum time, providing an appropriate radiation dose on each contact surface to be disinfected.

5. The method of claim 1, wherein step a) is directly performable by the data processing unit of the mobile robotic apparatus or is provided by a remote computer with respect to the mobile robotic apparatus and in communication therewith by a data communication network.

6. The method of claim 1, wherein step b) is directly performable by the data processing unit of the mobile robotic apparatus or is provided by a remote computer with respect to the mobile robotic apparatus and in communication therewith by a data communication network.

7. The method of claim 1, wherein the set operating features of the at least one UV-C radiation source comprise: surface, geometric arrangement, shape, and radiation power.

8. A mobile robotic apparatus for disinfecting a space, comprising:

a mobile base comprising a plurality of wheels;

at least one ultraviolet-C (UV-C) radiation source mounted on said mobile base;

a data processing unit operatively connected to the mobile base and to the at least one UV-C radiation source; and at least one first artificial vision sensor operatively connected to the data processing unit, said data processing unit being configured to:

acquire a map of the space to be disinfected;

acquire information on a plurality of contact surfaces to be disinfected within the space to be disinfected, each contact surface to be disinfected being associated with a criticality level with respect to which a related level of disinfection is to be ensured;

determine an amount of UV-C radiation energy to be deposited, by the at least one UV-C radiation source mounted on the mobile robotic apparatus, on a respective contact surface to be disinfected of said plurality of contact surfaces to be disinfected, said amount of UV-C radiation energy being determined as a function of the criticality level of the contact surface to be disinfected, of distance and orientation of the contact surface to be disinfected with respect to the at least one UV-C radiation source, and of set operating features of the at least one UV-C radiation source;

determine, for each time instant of a plurality of time instants, a respective virtual potential of attraction of the at least one UV-C radiation source towards each contact surface to be disinfected of said plurality of contact surfaces to be disinfected, by modulating over time the virtual potential of attraction of the at least one UV-C radiation source towards each contact surface to be disinfected of said plurality of contact surfaces to be disinfected as a function of the amount of UV-C radiation energy determined for each contact surface to be disinfected and radiated at a previous time instant, said virtual potential of attraction being a value of energy level determinable by a mathematical model representative of a law of attraction or repulsion towards each contact surface to be disinfected of said plurality of contact surfaces to be disinfected;

generate a path trajectory as a function of each determined virtual potential of attraction of the at least one UV-C radiation source towards each contact surface to be disinfected, the path trajectory being generated as directional speed or acceleration to be provided to the mobile robotic apparatus on the basis of each determined virtual potential of attraction of the at least one UV-C radiation source towards each contact surface to be disinfected, also comprising the energy stored by each contact surface to be disinfected in the previous transit of the mobile robotic apparatus; and control the mobile robotic apparatus along the generated path trajectory.

9. The mobile robotic apparatus of claim 8, comprising a plurality of odometry sensors, each odometry sensor of said plurality of odometry sensors being operatively associated with a wheel of said plurality of wheels, the plurality of odometry sensors being operatively connected to the data processing unit.

10. The mobile robotic apparatus of claim 8, further comprising at least one second artificial vision sensor operatively connected to the data processing unit.

11. The mobile robotic apparatus of claim 8, further comprising a data communication module operatively connected to the data processing unit of the mobile robotic apparatus, the data communication module being configured to be operatively connected to a remote computer of a user by a data communication network.

* * * * *